United States Patent
Skiba et al.

(10) Patent No.: US 6,723,107 B1
(45) Date of Patent: *Apr. 20, 2004

(54) METHOD AND APPARATUS FOR SUTURING

(75) Inventors: Jeffry B. Skiba, Santa Rosa, CA (US); Jeffrey P. Baldwin, Phoenix, AZ (US); Laird L. Hatch, Cave Creek, AZ (US); Gary M. Gartsman, Houston, TX (US); Ran Oren, Gaaton (IL)

(73) Assignee: Orthopaedic Biosystems Ltd., Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,975

(22) Filed: Apr. 18, 2000

Related U.S. Application Data

(60) Provisional application No. 60/129,993, filed on Apr. 19, 1999.

(51) Int. Cl.[7] ............................................. A61B 17/04
(52) U.S. Cl. ...................... 606/144; 606/222; 606/223
(58) Field of Search ................................ 606/222–227, 606/139, 144, 148; 112/222–227; 223/102

(56) References Cited

U.S. PATENT DOCUMENTS

| | | |
|---|---|---|
| 659,422 A | 10/1900 | Shidler |
| 818,152 A * | 4/1906 | Edwards ..................... 606/225 |
| 919,138 A | 4/1909 | Drake et al. |
| 1,635,066 A | 7/1927 | Wells |
| 1,815,725 A | 7/1931 | Pilling et al. |
| 2,065,659 A | 12/1936 | Cullen |
| 2,247,342 A | 6/1941 | Brown |
| 2,414,882 A | 1/1947 | Longfellow |
| 2,593,622 A | 4/1952 | Stanelle |
| 2,610,631 A | 9/1952 | Calicchio |
| 2,737,954 A | 3/1956 | Knapp |

(List continued on next page.)

FOREIGN PATENT DOCUMENTS

| | | |
|---|---|---|
| DE | 25 32 242 | 2/1977 |
| DE | 2532242 | 2/1977 |
| DE | 29722769 | 3/1998 |
| FR | 401199 | 8/1909 |
| GB | 528550 | 10/1940 |
| SU | 1034728 A | 8/1983 |
| WO | 95/02363 | 1/1995 |
| WO | WO 95/11630 | 5/1995 |
| WO | WO 96/39946 | 12/1996 |
| WO | WO 97/16121 | 5/1997 |
| WO | 99/12480 | 3/1999 |
| WO | 99/21507 | 5/1999 |

OTHER PUBLICATIONS

Charles V. Menendez, M.D., *A Revived Ligature Carrier*, The American Journal of Surgery, vol. 115, pp. 583–584, 1968.

Derek J. Byrne et al., *Highly selective vagotomy: use of a ligature carrier*, Annals of the Royal College of Surgeons of England, vol. 72, pp. 9–10, 1990.

(List continued on next page.)

*Primary Examiner*—Julian W. Woo
(74) *Attorney, Agent, or Firm*—Fish & Richardson P.C.

(57) ABSTRACT

Devices and techniques for suturing are particularly useful in laparoscopic, arthroscopic, and/or open surgical procedures. A method of delivering a suture includes providing a suture device, releasably coupling a suture to a distal end of a suture device by threading the suture through a first region of a bounded opening of the suture device and moving the suture to a second region of the bounded opening having a dimension smaller than a diameter of the suture to trap the suture in the second region, penetrating a substrate with the distal end of the suture device such that the a portion of the suture passes through the substrate, and releasing the suture from the distal end of the suture device.

20 Claims, 11 Drawing Sheets

U.S. PATENT DOCUMENTS

| | | | |
|---|---|---|---|
| 2,738,790 A | 3/1956 | Todt, Sr. et al. | |
| 2,880,728 A | 4/1959 | Rights | |
| 3,036,482 A | 5/1962 | Kenworthy et al. | |
| 3,470,834 A | 10/1969 | Bone | |
| 3,470,875 A | 10/1969 | Johnson | |
| 3,580,256 A | 5/1971 | Wilkinson et al. | |
| 3,638,653 A | 2/1972 | Berry | |
| 3,645,222 A * | 2/1972 | Zocher | 112/224 |
| 3,716,058 A | 2/1973 | Tanner, Jr. | |
| 3,840,017 A | 10/1974 | Violante | |
| 3,842,824 A | 10/1974 | Neufeld | |
| 3,842,840 A | 10/1974 | Schweizer | |
| 3,871,379 A | 3/1975 | Clarke | |
| 3,880,167 A * | 4/1975 | Hardwick | 606/222 |
| 3,890,975 A | 6/1975 | McGregor | |
| 3,892,240 A * | 7/1975 | Park | 606/222 |
| 3,901,244 A | 8/1975 | Schweizer | |
| 3,946,740 A | 3/1976 | Bassett | |
| 3,980,177 A | 9/1976 | McGregor | |
| 3,990,619 A | 11/1976 | Russell | |
| 4,161,951 A | 7/1979 | Scanlan, Jr. | |
| 4,164,225 A | 8/1979 | Johnson et al. | |
| 4,172,458 A | 10/1979 | Pereyra | |
| 4,224,947 A | 9/1980 | Fukuda | |
| 4,235,238 A | 11/1980 | Ogiu et al. | |
| 4,326,531 A | 4/1982 | Shimonaka | |
| 4,384,406 A | 5/1983 | Tischlinger | |
| 4,448,194 A | 5/1984 | DiGiovanni et al. | |
| 4,476,590 A | 10/1984 | Scales et al. | |
| 4,493,323 A | 1/1985 | Albright et al. | |
| 4,500,024 A | 2/1985 | DiGiovanni et al. | |
| 4,509,516 A | 4/1985 | Richmond | |
| 4,512,344 A | 4/1985 | Barber | |
| 4,535,768 A | 8/1985 | Hourahane et al. | |
| 4,563,961 A * | 1/1986 | Beyer et al. | 112/222 |
| 4,580,563 A | 4/1986 | Gross | |
| 4,590,929 A | 5/1986 | Klein | |
| 4,596,249 A | 6/1986 | Freda et al. | |
| 4,602,635 A | 7/1986 | Mulhollan et al. | |
| 4,615,705 A | 10/1986 | Scales et al. | |
| 4,621,639 A | 11/1986 | Transue et al. | |
| 4,621,640 A | 11/1986 | Mulhollan et al. | |
| 4,633,869 A | 1/1987 | Schmieding | |
| 4,641,652 A | 2/1987 | Hutterer et al. | |
| 4,643,178 A | 2/1987 | Nastari et al. | |
| 4,662,068 A | 5/1987 | Polonsky | |
| 4,716,893 A | 1/1988 | Fischer et al. | |
| 4,723,546 A | 2/1988 | Zagorski | |
| 4,724,840 A | 2/1988 | McVay et al. | |
| 4,739,751 A | 4/1988 | Sapega et al. | |
| 4,741,330 A | 5/1988 | Hayhurst | |
| 4,778,468 A | 10/1988 | Hunt et al. | |
| 4,779,616 A | 10/1988 | Johnson | |
| 4,787,377 A | 11/1988 | Laboureau | |
| 4,790,312 A | 12/1988 | Capuano, Sr. et al. | |
| 4,881,537 A | 11/1989 | Henning | |
| 4,890,615 A | 1/1990 | Caspari et al. | |
| 4,899,743 A | 2/1990 | Nicholson et al. | |
| 4,923,461 A | 5/1990 | Caspari et al. | |
| 4,935,027 A | 6/1990 | Yoon | |
| 4,950,285 A | 8/1990 | Wilk | |
| 4,957,498 A | 9/1990 | Caspari et al. | |
| 5,015,250 A | 5/1991 | Foster | |
| 5,037,433 A | 8/1991 | Wilk et al. | |
| 5,053,047 A | 10/1991 | Yoon | |
| 5,085,661 A | 2/1992 | Moss | |
| 5,100,418 A | 3/1992 | Yoon et al. | |
| 5,120,318 A | 6/1992 | Nallapareddy | |
| 5,123,913 A | 6/1992 | Wilk et al. | |
| 5,149,329 A | 9/1992 | Richardson | |
| 5,152,769 A | 10/1992 | Baber | |
| 5,174,087 A | 12/1992 | Bruno | |
| 5,178,629 A | 1/1993 | Kammerer | |
| 5,181,919 A | 1/1993 | Bergman et al. | |
| 5,201,744 A | 4/1993 | Jones | |
| 5,211,650 A | 5/1993 | Noda | |
| 5,217,471 A | 6/1993 | Burkhart | |
| 5,217,486 A | 6/1993 | Rice et al. | |
| 5,222,508 A | 6/1993 | Contarini | |
| 5,222,977 A * | 6/1993 | Esser | 606/223 |
| 5,224,955 A | 7/1993 | West | |
| 5,234,438 A | 8/1993 | Semrad | |
| 5,236,438 A | 8/1993 | Wilk | |
| 5,250,054 A | 10/1993 | Li | |
| 5,254,126 A | 10/1993 | Filipi et al. | |
| 5,259,846 A | 11/1993 | Granger et al. | |
| 5,266,075 A | 11/1993 | Clark et al. | |
| 5,269,783 A | 12/1993 | Sander | |
| 5,269,786 A | 12/1993 | Morgan | |
| 5,281,234 A | 1/1994 | Wilk et al. | |
| 5,281,237 A | 1/1994 | Gimpelson | |
| 5,282,809 A | 2/1994 | Kammerer et al. | |
| 5,306,280 A | 4/1994 | Bregen et al. | |
| 5,312,422 A | 5/1994 | Trott | |
| 5,327,896 A | 7/1994 | Schmieding | |
| 5,330,486 A | 7/1994 | Wilk | |
| 5,334,198 A | 8/1994 | Hart et al. | |
| 5,336,231 A | 8/1994 | Adair | |
| 5,356,419 A | 10/1994 | Chow | |
| 5,364,408 A | 11/1994 | Gordon | |
| 5,372,604 A | 12/1994 | Trott | |
| 5,382,257 A | 1/1995 | Lewis et al. | |
| 5,383,883 A | 1/1995 | Wilk et al. | |
| 5,391,170 A | 2/1995 | McGuire et al. | |
| 5,391,173 A | 2/1995 | Wilk | |
| 5,391,174 A | 2/1995 | Weston | |
| 5,393,302 A | 2/1995 | Clark et al. | |
| 5,405,354 A * | 4/1995 | Sarrett | 606/148 |
| 5,409,494 A | 4/1995 | Morgan | |
| 5,441,502 A | 8/1995 | Bartlett | |
| 5,441,507 A | 8/1995 | Wilk | |
| 5,447,512 A | 9/1995 | Wilson et al. | |
| 5,449,367 A | 9/1995 | Kadry | |
| 5,456,246 A | 10/1995 | Schmieding et al. | |
| 5,464,425 A | 11/1995 | Skiba | |
| 5,466,243 A | 11/1995 | Schmieding et al. | |
| 5,496,331 A | 3/1996 | Xu et al. | |
| 5,501,688 A | 3/1996 | Whiteside et al. | |
| 5,520,696 A | 5/1996 | Wenstrom, Jr. | |
| 5,520,703 A | 5/1996 | Essig et al. | |
| 5,522,820 A | 6/1996 | Caspari et al. | |
| 5,527,322 A | 6/1996 | Klein et al. | |
| 5,545,170 A | 8/1996 | Hart | |
| 5,549,613 A | 8/1996 | Goble et al. | |
| 5,549,618 A | 8/1996 | Fleenor et al. | |
| 5,549,636 A | 8/1996 | Li | |
| 5,554,171 A | 9/1996 | Gatturna et al. | |
| 5,562,683 A | 10/1996 | Chan | |
| 5,562,685 A | 10/1996 | Mollenauer et al. | |
| 5,562,687 A | 10/1996 | Chan | |
| 5,562,696 A | 10/1996 | Nobles et al. | |
| 5,565,122 A | 10/1996 | Zinnbauer et al. | |
| 5,569,269 A | 10/1996 | Hart et al. | |
| 5,571,090 A | 11/1996 | Sherts | |
| 5,571,119 A | 11/1996 | Atala | |
| 5,601,571 A | 2/1997 | Moss | |
| 5,618,304 A | 4/1997 | Hart et al. | |
| 5,626,590 A | 5/1997 | Wilk | |
| 5,632,748 A | 5/1997 | Beck, Jr. et al. | |
| 5,643,266 A | 7/1997 | Li | |
| 5,645,552 A | 7/1997 | Sherts | |

| | | |
|---|---|---|
| 5,658,299 A | 8/1997 | Hart |
| 5,662,658 A | 9/1997 | Wenstrom, Jr. |
| 5,665,096 A | 9/1997 | Yoon |
| 5,681,333 A | 10/1997 | Burkhart et al. |
| 5,690,677 A | 11/1997 | Schmieding et al. |
| 5,693,061 A | 12/1997 | Pierce et al. |
| 5,697,950 A | 12/1997 | Fucci et al. |
| 5,709,692 A | 1/1998 | Mollenauer et al. |
| 5,728,135 A | 3/1998 | Bregen et al. |
| 5,749,376 A | 5/1998 | Wilk et al. |
| 5,752,964 A | 5/1998 | Mericle |
| 5,792,152 A | 8/1998 | Klein et al. |
| 5,797,927 A | 8/1998 | Yoon |
| 5,800,447 A | 9/1998 | Wenstrom, Jr. |
| 5,814,052 A | 9/1998 | Nakao et al. |
| 5,814,054 A | 9/1998 | Kortenbach et al. |
| 5,817,108 A | 10/1998 | Poncet |
| 5,826,776 A | 10/1998 | Schulze et al. |
| 5,827,298 A | 10/1998 | Hart et al. |
| 5,843,084 A | 12/1998 | Hart et al. |
| 5,843,099 A | 12/1998 | Nichols et al. |
| 5,846,254 A | 12/1998 | Schulze et al. |
| 5,855,311 A | 1/1999 | Hamblin et al. |
| 5,860,983 A | 1/1999 | Wenstrom, Jr. |
| 5,897,563 A | 4/1999 | Yoon et al. |
| 5,897,564 A | 4/1999 | Schulze et al. |
| 5,897,574 A | 4/1999 | Bonutti |
| 5,904,692 A | 5/1999 | Steckel et al. |
| 5,906,620 A | 5/1999 | Nakao et al. |
| 5,908,426 A | 6/1999 | Pierce |
| 5,918,604 A | 7/1999 | Whelan |
| 5,928,252 A | 7/1999 | Steadman et al. |
| 5,941,439 A | 8/1999 | Kammerer et al. |
| 5,944,724 A | 8/1999 | Lizardi |
| 5,951,559 A | 9/1999 | Burkhart |
| 5,968,047 A | 10/1999 | Reed |
| 5,980,557 A | 11/1999 | Iserin et al. |
| 5,993,451 A | 11/1999 | Burkhart |
| 5,993,466 A | 11/1999 | Yoon |
| 6,006,965 A * | 12/1999 | Hamann ................. 223/102 |
| 6,010,513 A | 1/2000 | Tormala |
| 6,039,753 A | 3/2000 | Meislin |
| 6,045,561 A | 4/2000 | Marshall et al. |
| 6,071,289 A | 6/2000 | Stefanchik et al. |
| 6,074,403 A | 6/2000 | Nord |
| 6,096,060 A | 8/2000 | Fitts et al. |
| 6,099,538 A | 8/2000 | Moses et al. |
| 6,113,610 A | 9/2000 | Poncet |
| 6,132,433 A | 10/2000 | Whelan |
| 6,146,387 A | 11/2000 | Trott et al. |

OTHER PUBLICATIONS

Fred S. Miyazaki, MD, *MIYA Hook Ligature Carrier For Sacrospinous Ligament Suspension*, The American College of Obstetricians and Gynecologists, vol. 70, No. 2, Aug. 1987.

G. Lichtenberger et al., *Laryngomikrochirurgische Laterofixation gelahmter Stimmlippen mit Hilfe eines neuen Nahtinstrumentes*, Laryngo–Rhino–Otol., 68(1989), pp. 678–682.

H. Courtenay Clarke, M.D., *Laparoscopy—New Instruments for Suturing and Ligation*, Fertility and Sterility,, vol. 23, No. 4, pp. 274–277, Apr. 1972.

Harrith M. Hasson, M.D., *Suture Loop Techniques to Facilitate Microsurgical and Laparascopic Procedures*, The Journal of Reproductive Medicine for the Obstetrician and Gynecologist, vol. 32, pp. 765–767, No. 10/Oct. 1987.

Linvatec 1994 Product Catalog, pp. 59 and 61, Linvatec Corporation (1994).

Rene D. Esser, M.D., *Arthroscopic Meniscus Repair: The Easy Way*, The Journal of Arthroscopic and Related Surgery, 9(2), pp. 231–233, 1993.

V. John Kilejian, *"The Suturer": A New Suturing Instrument*, The Journal of Urology, vol. 133, pp. 231–232, Feb. 1985.

* cited by examiner

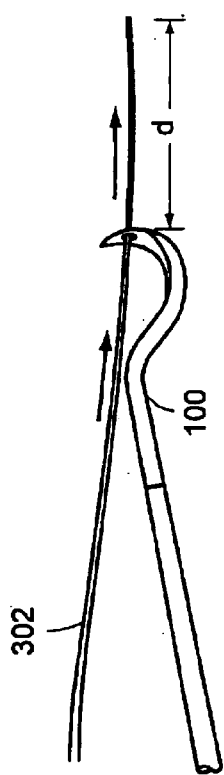
FIG. 3
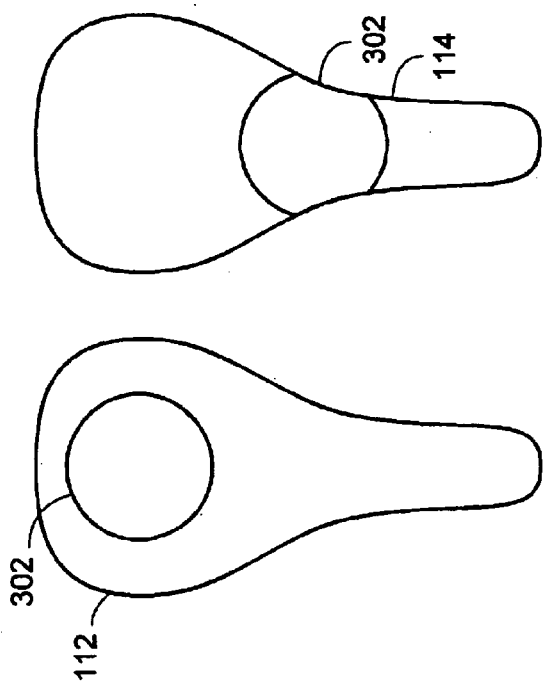
FIG. 4
FIG. 6A
FIG. 6B
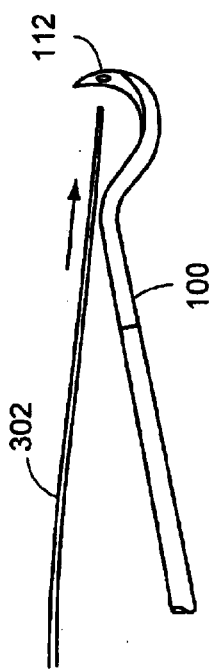
FIG. 5

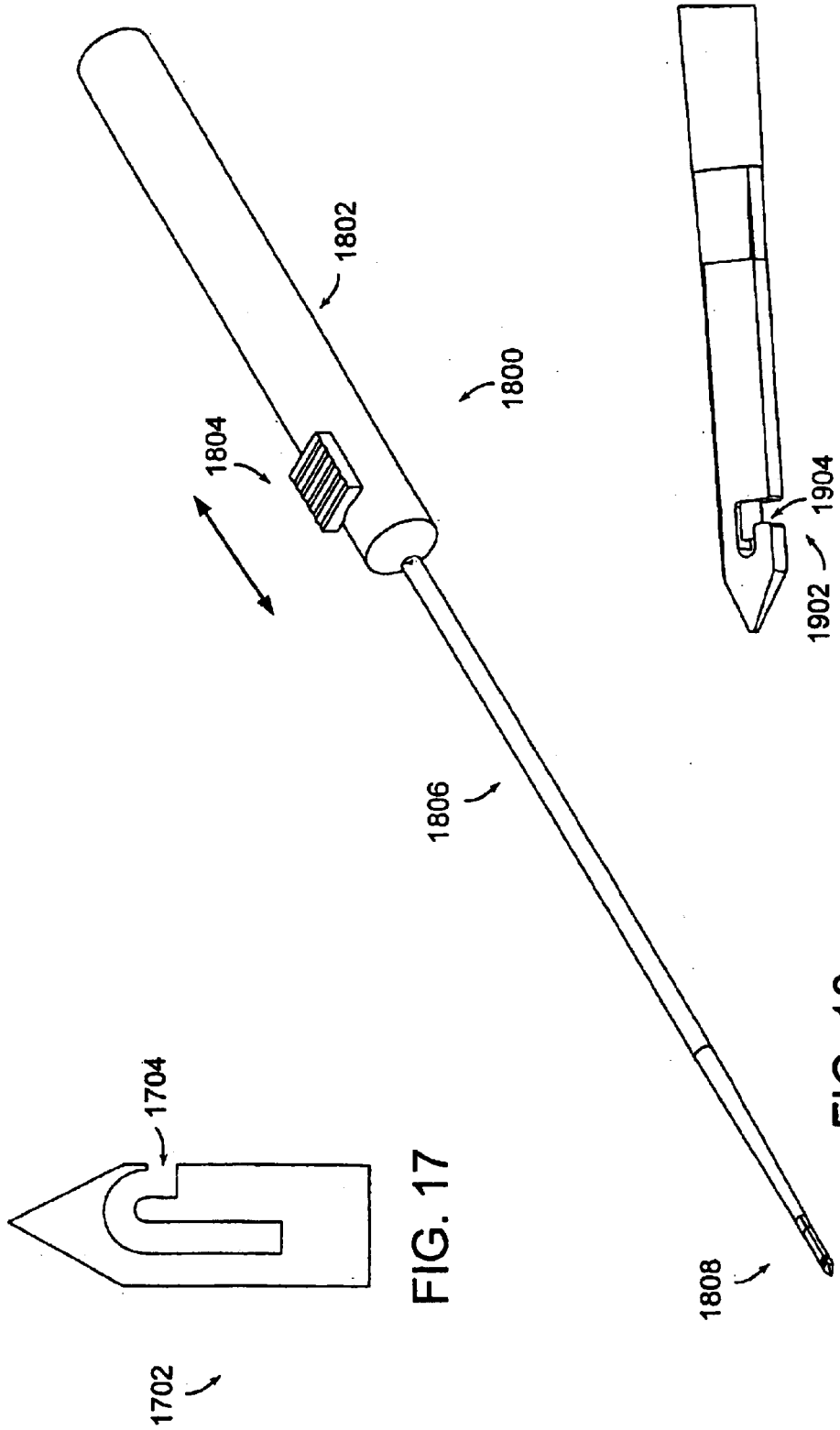

METHOD AND APPARATUS FOR SUTURING

RELATED APPLICATION/CLAIM OF PRIORITY

This Application is related to and claims priority from Provisional Application Ser. No. 60/129,993 entitled "Suture Leader for Shuttleless suturing", filed Apr. 19, 1999.

FIELD OF INVENTION

The present invention relates to methods and apparatus for use in surgical suturing.

BACKGROUND OF INVENTION

Suture is often used bring two pieces of tissue together and hold the tissues as they heal. Needles allow a surgeon to pierce tissue and pull suture through that tissue. In many procedures, there is adequate space in the wound or incision to manipulate needles and needle holding instruments. The move by surgeons toward less invasive and minimally invasive surgeries has created the need for instruments to be designed to function in limited space and with longer reaches. Standard surgical instruments are being stretched and downsized to pass through tunnels in the tissue called cannulas or portals measuring as small as 5 millimeters in diameter and in a variety of lengths. There is a need for improved surgical instruments to manipulate and control sutures during surgical operations.

SUMMARY OF THE INVENTION

The present invention provides new and useful devices and techniques for use in suturing. These devices and techniques are particularly useful in laparoscopic, arthroscopic, and/or open surgical procedures.

One type of suturing device according to the invention is characterized by a handle with an elongated shaft with a sharpened tip configured to hold a suture at a selected point on the suture. Several different types of structures for holding the suture to the sharp tip are provided according to the principles of the invention. For example, one such structure comprises a tapered opening formed in the tip, and configured to enable a suture to be wedged and held in the opening. In another example, an elongated opening is provided, which may be curved, for holding the suture. In yet another example, a locking mechanism is provided, which has a locked position for holding the suture, an unlocked position for releasing the suture, and a partially locked position for controlled adjustment of the suture position relative to the tip.

Another type of device according to the principles of the invention is characterized by new and useful structures and techniques for loading the suture into the device. In one example of this aspect of the present invention, a suture may be side-loaded into the device. This provides numerous advantages, including eliminating the need to thread the suture, and allowing side-release of the suture.

According to still another aspect of the present invention, different shaped suture tips are provided for the selection of the most effective tip shape for a given application. In one example of this aspect of the present invention, each tip may be detached from the suturing device and replaced by another tip. In another example of this aspect of the present invention, the position of each tip is adjustable relative to the shaft of the suturing device for further refinement of the suturing device for a given application.

A suturing device according to the present invention may also be configured for use with a needle point swaged to a suture.

Yet another type of suturing device according to the principles of present invention includes a tissue support structure disposed adjacent the sharpened tip, which may move relative to the sharpened tip to facilitate penetration of the tip through a tissue. In one example of this aspect of the present invention, a suture is carried through the tissue by the tip as the tip penetrates the tissue. In another example of this aspect of the present invention, the tip engages the suture after penetration of the tissue, and draws the suture through the tissue as the tip is withdrawn from the tissue.

A method according to the present invention is characterized by releasably coupling a suture to a suture device, causing the tip of the suture device and a portion of the suture to penetrate a tissue, and releasing the suture from the suture device, so the suture may be drawn through the tissue for completion of a suturing procedure.

These and other features and techniques of the present invention will become further apparent from the following detailed description and the accompanying drawings.

BRIEF DESCRIPTION OF THE DRAWINGS

A more complete understanding of the present invention may be derived by referring to the detailed description and claims when considered in connection with the following illustrative Figures, which may not be to scale. In the following Figures, like reference numbers refer to similar elements throughout the Figures.

FIGS. 3–5 illustrate the relative positions of a suture and a suturing device during coupling of a suture with the suturing device in accordance with the principles of the present invention;

FIGS. 6A–6B schematically illustrate the manner in which a suture is trapped and held by an opening in the sharpened tip of a suturing device in accordance with the principles of the present invention;

FIGS. 11–17 schematically illustrate sharpened tips and different configurations for an opening for use in coupling a suture with the sharpened tip in accordance with the principles of the present invention;

FIGS. 18–21 schematically illustrate a suturing device with a locking mechanism according to the principles of the present invention;

DETAILED DESCRIPTION

As set forth above, the present invention provides several types of devices and techniques which are useful in suturing, for example in connection with laparoscopic, arthroscopic, and/or open surgical procedures. Examples of devices and techniques according to the principles of the present invention are described below in connection with particular embodiments, but it will be clear to those skilled in the art that aspects of the present invention found in one example may be practiced alone or in combination with (or even in lieu of) devices and techniques of the other examples.

Figure 1:
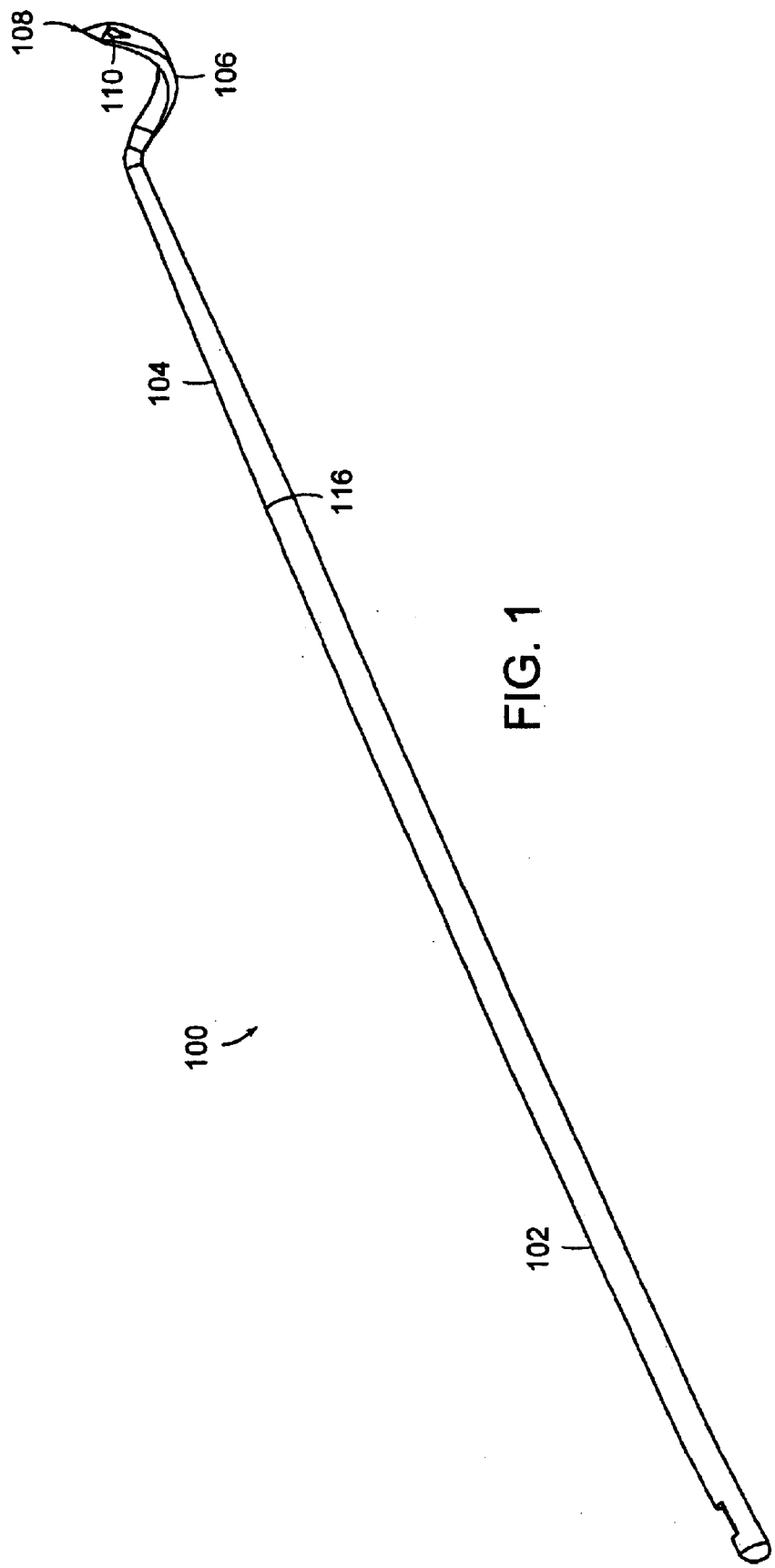
FIG. 1 is a perspective view of a suturing device in accordance with the present invention.

One type of suturing device in accordance with the present invention is shown in FIG. 1. Suturing device 100 has a handle 102, a shaft 104 connected to the handle, and a tip 106 connected to the other (distal) end of the shaft. Typically, the handle 102 may be 4 to 6 inches long, and the shaft 104 may typically be from 1 to 24 inches, depending on the application. The shaft is typically 2 to 3 millimeters in diameter and formed of a rigid substance Tip 106 includes a sharpened point 108 and an eyelet (or opening) 110.

Figure 2:
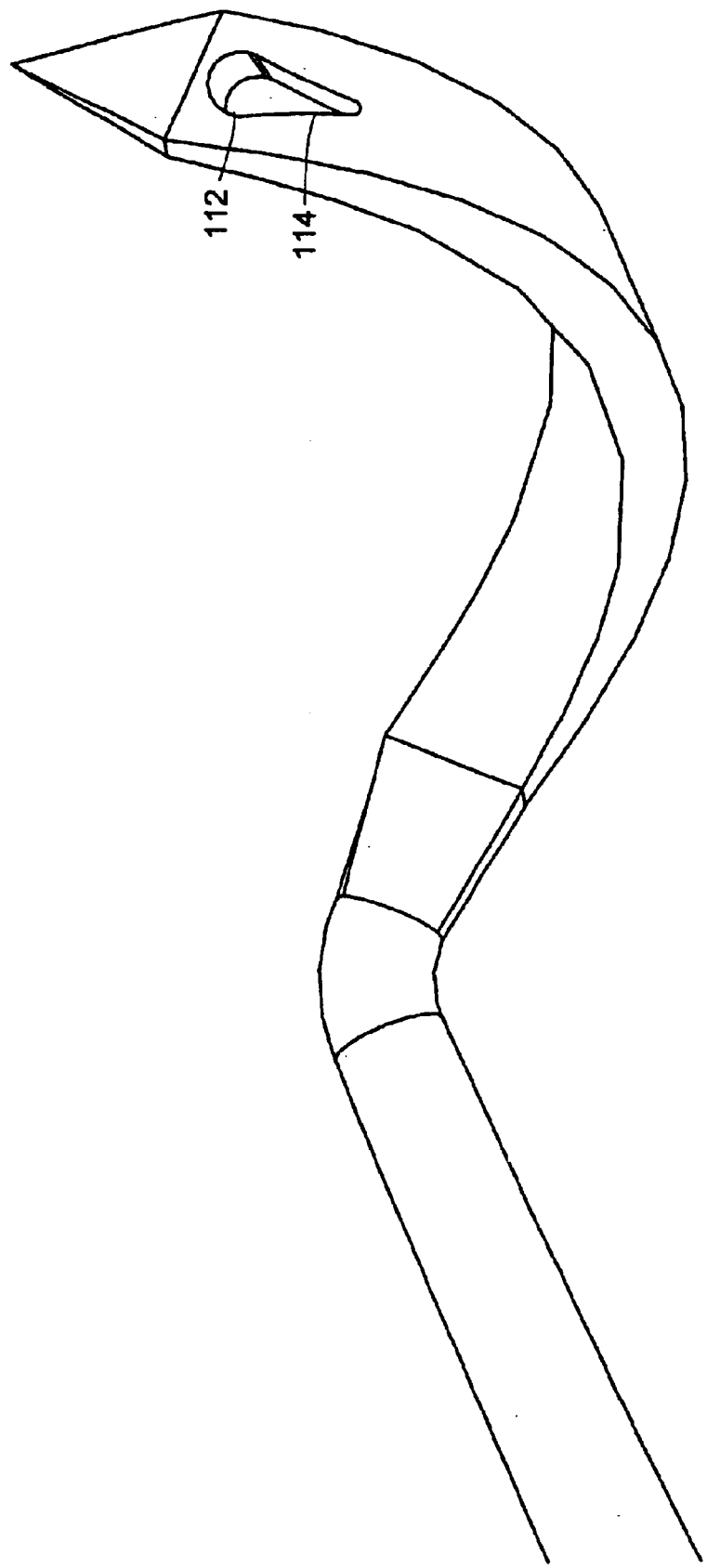
FIG. 2 is a close-up perspective view of the sharpened tip at the distal end of the suturing device of FIG. 1.

FIG. 2 shows a close-up view of tip 106. Tip 106 has a curved, hook-like shape for convenient delivery of a suture, as discussed further below. Eyelet 110 has a tip portion 112 configured to be wider than a suture used in connection with the suturing device, and a narrowed bottom portion 114 for trapping the suture.

Referring now to FIGS. 3 through 6B, a method according to the present invention is shown. Suture 302 is threaded through eyelet 110 as shown in FIGS. 3 and 4 until a selected length of suture (labeled "d") is extended through suturing device 100 as shown in FIG. 4. Preferably, length d is about 2 inches. Once the selected point of suture is in eyelet 110, length d is drawn downward, as shown in FIG. 5, trapping the suture in eyelet 110. FIG. 6A shows the position of the suture in the wider top portion 112 of eyelet 110 prior to the drawing downward step. FIG. 6B shows the suture wedged into the narrowed bottom portion 114 of eyelet 110 after the downward drawing step of FIG. 5. The suture in FIG. 6B is thus trapped in the narrowed bottom portion 114 in accordance with one aspect of the invention.

Figure 8:
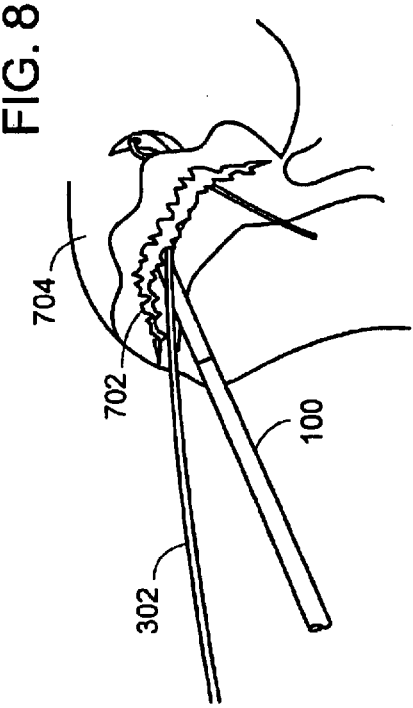
FIGS. 7–10 illustrate successive steps in applying a suture to tissue using a suturing device in accordance with the principles of the present invention.
Figure 10:
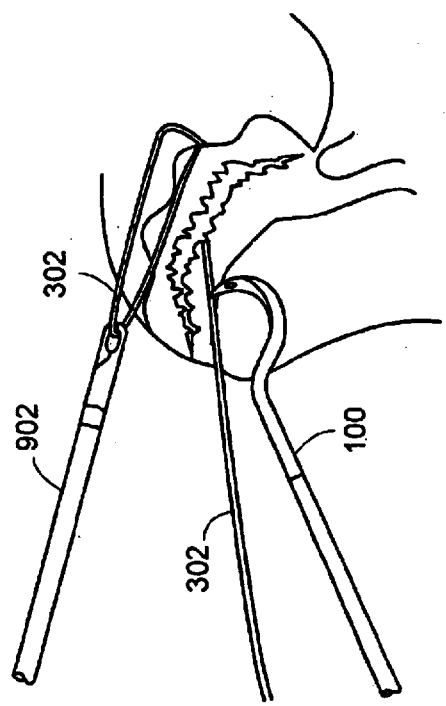
Figure 7:
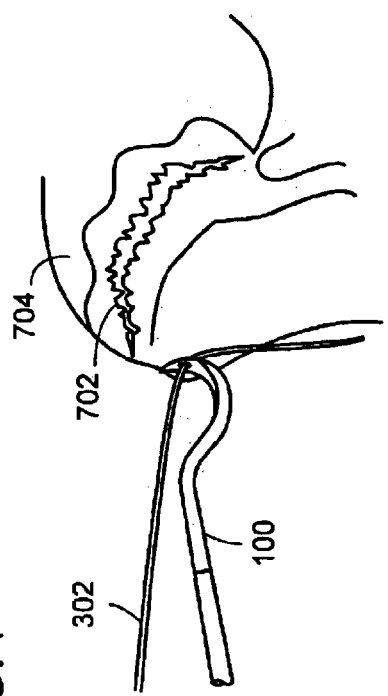
Figure 9:
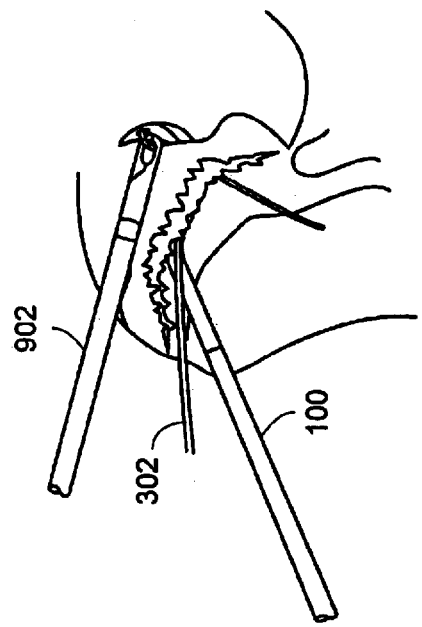

FIGS. 7 through 10 show use of the above described embodiment of the present invention in the repair of a gap 702 formed in tissue 704. As shown in FIGS. 7 and 8, suturing device 100 with suture 302 is partially inserted into a portion of tissue 704. Sharpened tip 106 of suturing device 100 penetrates tissue 704, thereby delivering suture 302 to the other side of tissue 704. A second tool 902 (FIG. 9) is used to assist in the release of suture 302 from eyelet 110, and to draw the short end of suture 302 the rest of the way through tissue 704 and fully disengage suture 302 from device 100 (See FIG. 10). Exhibit A shows color illustrations similar to FIGS. 7 through 10 and which may more clearly illustrate the contrast between the tool, the suture, and the tissue that is being sutured.

Figure 11:
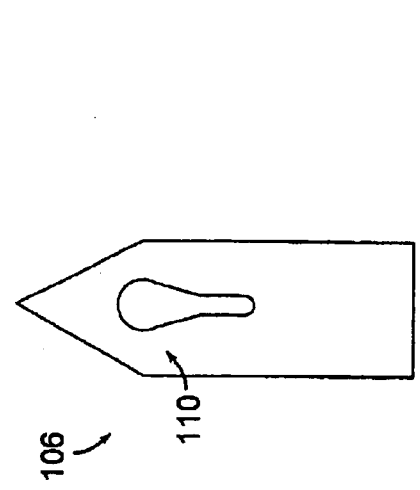

FIG. 11 shows a close-up of a tapered eyelet 110 of the type described in FIGS. 1 through 10, and further illustrates the orientation of the tapered eyelet 110 relative to the sharpened tip 106.

Figure 12:
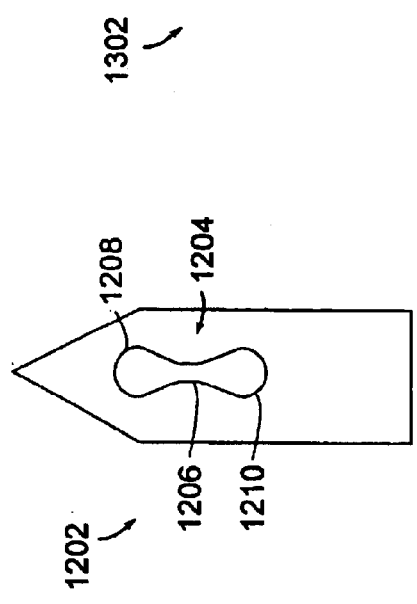

FIG. 12 shows a close-up of a sharpened tip 1202 with an alternative embodiment of an eyelet 1204 in accordance with the principles of the present invention. Eyelet 1202 has a tapered central portion 1205 which may trap a suture from either the top wider portion 1208 or the bottom wider portion 1210 of eyelet 1204. One advantage of this embodiment is that the device operator may disengage suture 302 from device 100 either by pulling the suture towards the wider top portion 1208 or the wider bottom portion 1210. It will be clear to one skilled in the art that this embodiment of the present invention provides added flexibility in the manner in which the suture can be released.

Figure 13:
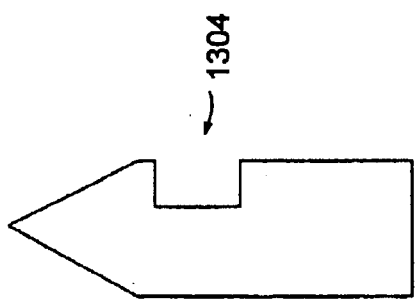

FIG. 13 shows a close-up of a sharpened tip 1302 with another alternative embodiment of an eyelet 1304 in accordance with the principles of the present invention. Eyelet 1304 is configured for side-loading of the suture into the eyelet. Eyelet 1304 is advantageous where the end of a suture is frayed, or it is otherwise difficult or time-consuming to pass lengthwise through an eyelet (as shown in FIGS. 3 and 4). The eyelet configuration shown in FIG. 13 allows for very easy loading, sliding, and release of the suture from the suturing device.

Figure 14:
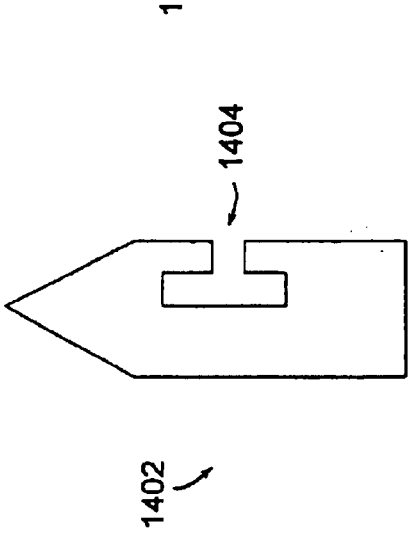

FIG. 14 shows another sharpened tip 1402 with still another embodiment of an eyelet 1404 with the feature of side-loading of a suture according to the principles of the present invention. The T-shaped configuration of eyelet 1404 substantially traps the suture in eyelet 1404 while allowing the suture to slide lengthwise through the eyelet.

Figure 15:
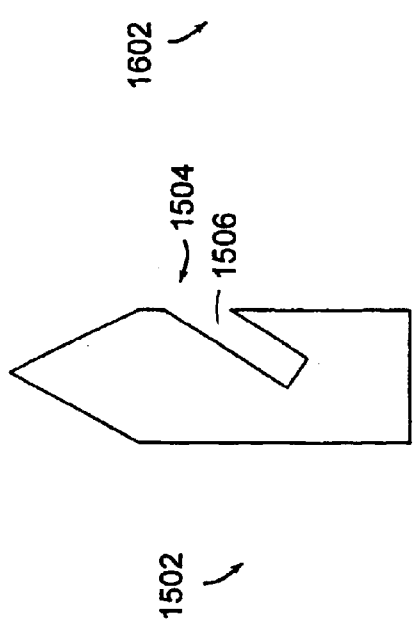

FIG. 15 shows yet another sharpened tip 1502 with another configuration of an eyelet 1504 with side-loading capability according to the principles of the present invention. Eyelet 1504 is configured with a deep diagonal slot 1506 which substantially traps the suture while allowing the suture to slide lengthwise through the eyelet.

Figure 16:
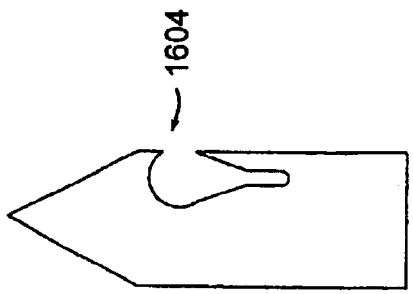

FIG. 16 shows yet another sharpened tip 1602 with another embodiment of an eyelet 1604 with side-loading capability according to the principles of the present invention. In FIG. 16, eyelet 1604 has a tapered configuration so that a suture may be side-loaded into a suturing device and then wedged into the tapered portion of the eyelet for improved trapping of the suture.

FIG. 17 shows yet another sharpened tip 1702 with another embodiment of an eyelet 1704 with a side-loading capability according to the principles of the present invention. In FIG. 17, eyelet 1704 has an elongated and curved configuration for substantially trapping a suture while allowing the suture to slide lengthwise through the eyelet. The elongated and curved configuration of the eyelet makes it very unlikely that a suture will be unintentionally released from the suturing device.

FIGS. 18 through 21 illustrate a suturing device with a locking mechanism for trapping a suture in an opening in a sharpened tip in accordance with the principles of the present invention. As shown in FIG. 18, suturing device 1800 has a handle 1802 with locking mechanism button 1804, shaft 1806, and sharpened tip 1808.

FIG. 19 illustrates a close-up of sharpened tip 1808, having opening 1902 and locking element 1904. Locking element 1904 is controlled by the device operator with button 1804 (FIG. 18). Locking element 1804 may be selectively placed in (1) an open position for inserting a suture into an opening in the sharpened tip and for release of the suture from the opening in the sharpened tip; (2) at least one partially closed position for capturing the suture and for controlled adjustment of the suture relative to the tip; and (3) a locked position for trapping a suture in the opening in the sharpened tip at a selected point.

Figure 20:
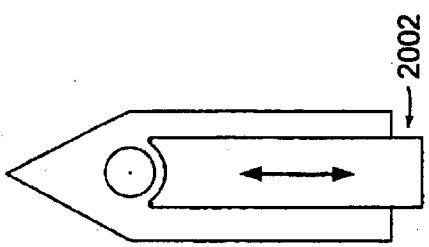
Figure 23:
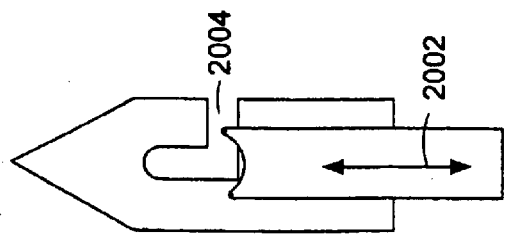

FIG. 20 further illustrates the use of the locking mechanism in accordance with the principles of the invention. FIG. 20 shows a schematic view of the sharpened tip 1808 with opening 1902. Sharpened tip 1808 has side-loading capability and locking element 1904, which can be selectively placed in any of the foregoing positions by movement of the locking element in the direction of arrow 2002. When a suture is first side-loaded, locking element 1904 is in the open position as shown in FIG. 20. As locking element 1904 is pushed forward and the side-opening 2004 is blocked-off, the suture is captured in the tip, but is not yet trapped in a particular position. In this state, the suture may slide lengthwise relative to sharpened tip 1808, but may not be removed from sharpened tip 1808 unless the full length of the the suture is drawn through opening 1902. As element 1904 is moved further forward, it engages the suture with a light amount of friction, giving the device operator the ability to control the lengthwise movement of the suture without damaging the suture. Finally as locking element 1904 is pushed fully forward, the suture becomes wedged in opening 1902, and fixed in a locked position. Release of the suture is achieved by moving the locking button to move the locking element away from the locked position.

Figure 21:
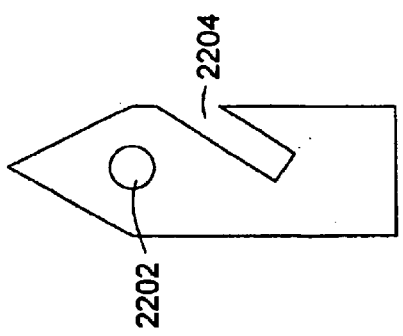

In the embodiment of the present invention shown in FIG. 21, the locking element moves in the same manner as in FIG. 20, and the same locking principles apply, but no side-loading capability is provided.

Figure 22:
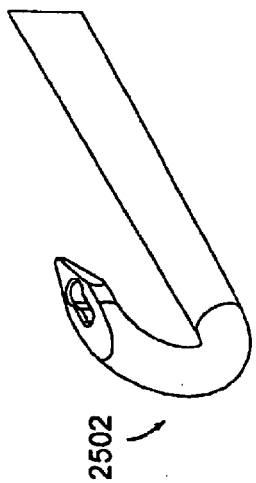
FIG. 22 schematically illustrates a sharpened tip with a combination of openings for use in coupling a suture with the sharpened tip in accordance with the principles of the present inventions.

Referring to FIG. 22, various combinations of eyelets may be formed on a sharpened tip in accordance with the principles of the present invention. For example, a round eyelet 2202 may be formed in addition to a deep diagonal slot 2204 on a device tip to allow selection of fully enclosing a suture (round eyelet) or side-loading of a suture with substantial trapping of the suture (deep diagonal slot) on the same tool. As another example, the eyelet with a tapered central portion as shown in FIG. 12 may also be combined with a side-loading feature. These and other combinations in accordance with the principles of the invention are intended to be included within the scope of the present invention.

Figure 25:
FIGS. 23–29 schematically illustrate different configurations for a sharpened tip with an opening for coupling a suture with the sharpened tip in accordance with the principles of the present invention.
Figure 24:
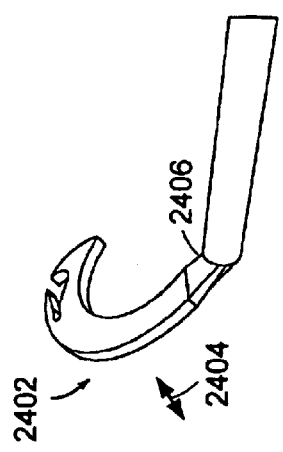

FIGS. 23 through 29 show different sharpened tips for use in different-applications of the present invention. The sharpened tip 2302 illustrated in FIG. 23 extends substantially straight, forward from the distal end of the device shaft. Alternatively, as shown in FIG. 24, a sharpened tip 2402 may be bent relative to the shaft in a selected direction, and angled to a side. As illustrated in FIG. 25, a sharpened tip 2502 may be bent so that the distal portion of the tip generally points towards the proximal end of the shaft.

Figure 26:
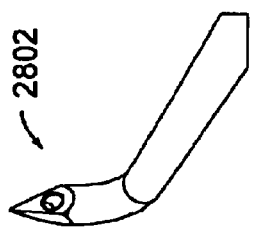

Referring now to FIG. 26, an alternative embodiment according the present invention is shown wherein a sharpened tip 2602 is curved at least partially about the distal end of the shaft.

Figure 27:
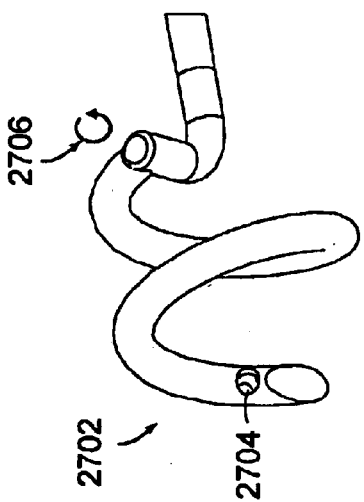

In a further embodiment according to FIG. 27, a sharpened tip 2702 is formed with at least one spiral loop at the distal end of the shaft. In the illustrated example, the spiral shaped tip 2702 has about 1.5 loops. According to this embodiment of the present invention, with a suture held near the front of the spiral (see location of eyelet 2704), the suture may be passed through a tissue two or more times prior to releasing the stitch from a suturing device.

Figure 28:
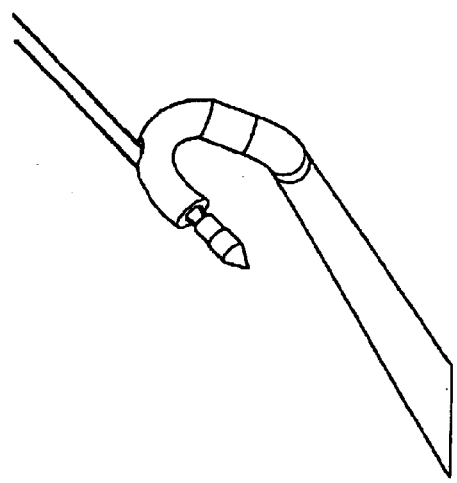

As shown in FIG. 28, a sharpened tip 28 may be configured to extend directly to one side of the distal end of the shaft.

Figure 29:
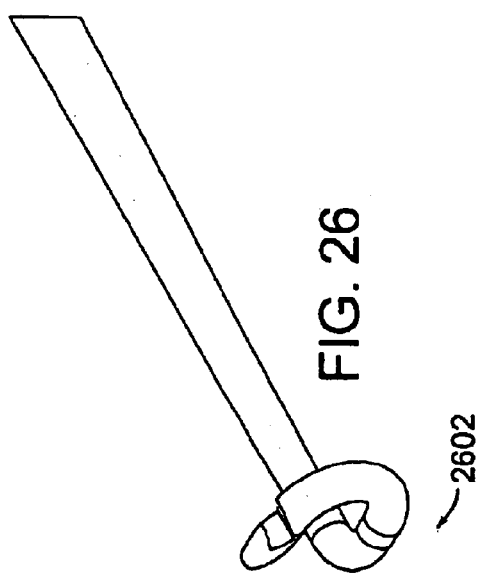

Further, as shown in FIG. 29, a sharpened tip 2902 may be configured to extend at least partially forward from the distal end of the shaft with a concave configuration.

Each of the above sharpened tip configurations may be selected for a particular application to allow a surgeon to pierce tissue in precisely the position chosen for the optimal re-approximation of tissue. Further, each of the above sharpened tip configurations may be combined with the other various aspects of the present invention to provide a wide selection of combinations to best pass suture through a substrate. For example, each of the above sharpened tip configurations may be combined with any of the eyelet configurations. Moreover, any of the eyelets could have side-loading capability and/or a locking mechanism.

In accordance with a further principle of the present invention, each tip may be configured for adjustability relative to the axis of the suturing device shaft, for providing further flexibility as to the orientation in which the suture may be applied to a gap in tissue. For example, the angle of the tip in FIG. 24 relative to the shaft may be adjusted at point in the direction of arrow 2404. Similarly, the looped tip in FIG. 27 may be rotated in the direction of arrow 2706. Each of the sharpened tips disclosed thus may be pivoted, rotated, or otherwise further adapted for improved application of the sharpened tip and the suture.

In accordance with a further principle of the present invention, various tips may be removed from the suturing device and replaced with an alternative tip or with a new, sharper tip. For example, referring to FIG. 24, the tip may be removed at point 2406 and replaced with the tip as shown in FIG. 25. Alternatively, the tip may be detached at other positions on the suturing device, such as by removing the shaft at point 116 (FIG. 1), and replacing it with a shaft carrying a differently shaped tip.

Figure 30:
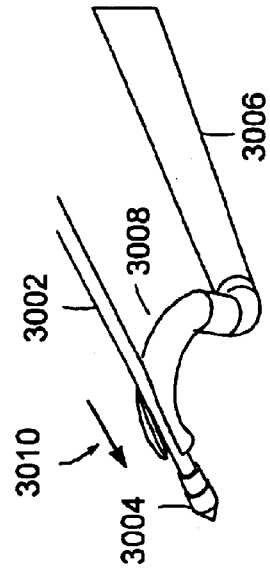
FIGS. 30–32 schematically illustrate different ways for coupling a needle with a swaged suture to a suturing device in accordance with the principles of the present invention.
Figure 31:
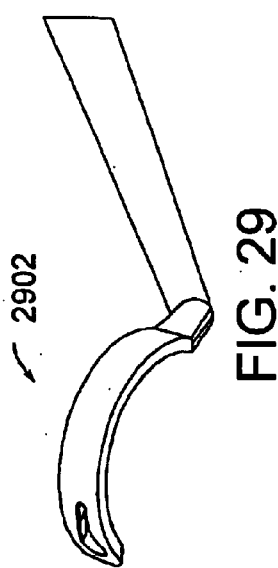
Figure 32:
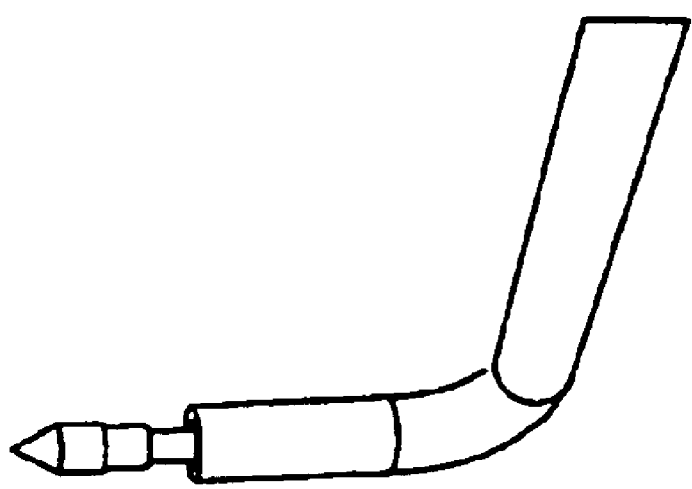

Referring now to FIGS. 30 through 32, further embodiments of the present invention configured for use with a needle point swaged to a suture are shown. As shown in FIG. 30, suture 3002 with needle tip 3004 may be side-loaded into a suturing device with a shaft 3006 with a curved distal end portion 3008. In accordance with this aspect of the invention, needle tip 3004 is sharpened and acts to penetrate and lead suture 3002 through a tissue. Once the tissue is punctured, the needle tip is grasped with a suture grasper (e.g. similar to second tool 902 in FIG. 9) and removed from the shaft in the direction of arrow 3010. The shaft is withdrawn and the suture is pulled through the tissue to complete the stitch. This embodiment also allows the simple replacement of sharp needles for tips that may have become dull. Further, tissue abrasion associated with pulling the short end of a suture through an opening already containing a length of suture is eliminated.

The shaft as in FIG. 30 may be modified as a cannula with the suture passing through a partial length of the device (FIG. 31) or the full length of the device (FIG. 32). These structures are advantageous in reducing or eliminating the amount of loose suture from the procedure area. Each of the devices in FIGS. 30 through 32 will preferably have a configuration for firmly holding the needle tip while it is piercing the tissue.

Figure 33:
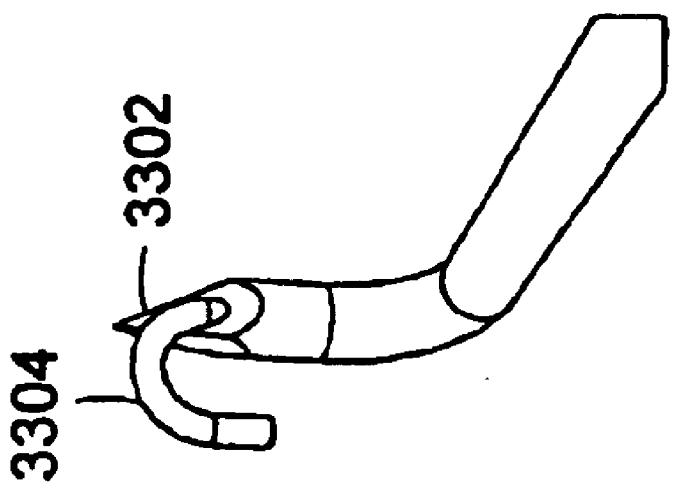
FIG. 33 schematically illustrates another way for coupling a suture to a suturing device in accordance with the principles of the present invention.

Referring to FIG. 33, alternatively, a suturing device 3300 may have a sharpened tip 3302, as in FIGS. 1 through 29, and be configured as a cannula with the suture passing through the full length of the device with a section 3304 protruding from the tip, in position for grasping as soon as the sharpened tip pierces a substrate. Section 3304 is located behind the first portion of the tip sharpened tip that pierces a tissue, so that the outwardly extending portion is carried through the tissue which has been pierced by the sharpened tip.

Figure 34:
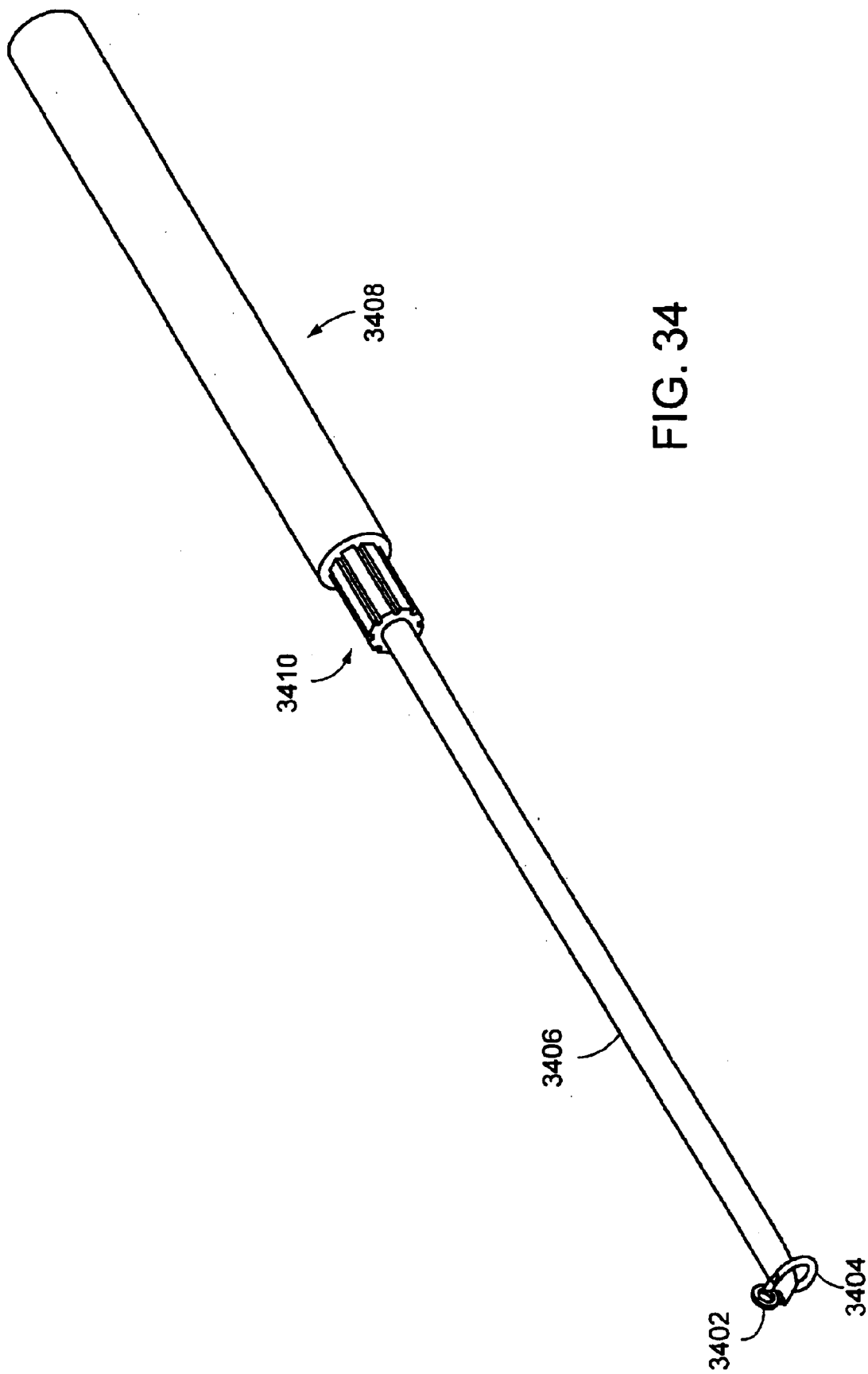
FIG. 34–36 illustrate a suture device in which a tissue support device is provided in accordance with the principles of the present invention.
Figure 35:
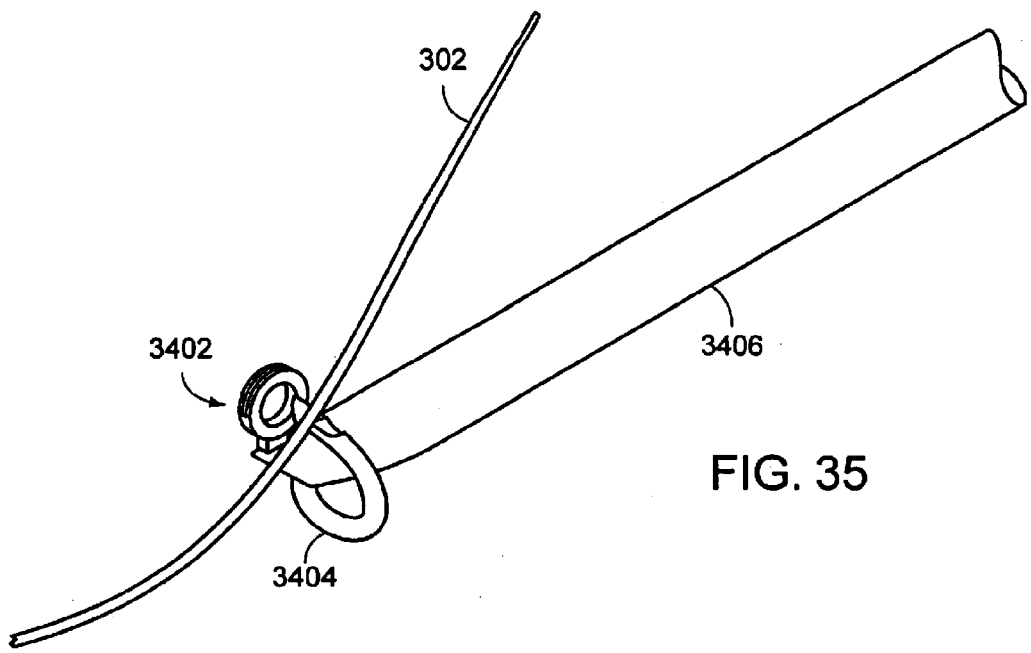

Referring now to FIG. 34, another embodiment of the invention including a tissue support structure 3402 disposed adjacent sharpened tip 3404 is shown (Exhibit B is a color illustration similar to FIG. 34, but also showing a suture). Tissue support structure 3402 is located on rotatable sheath 3406, which encases a shaft (shaft is not shown but is attached to handle 3408 and tip 3404). Rotatable sheath 3406 is preferably rotated by turning serrated handle 3410. Referring briefly to FIG. 35, a close-up view of the distal tip of a suturing device according to the principles of FIG. 34 is shown.

On occasion, the tissue to be sutured is difficult to pierce and requires pressure from behind to "push" the tissue against the sharpened tip. Use of tissue support structure 3402 is accomplished by positioning a portion of tissue to be sutured in between sharpened tip 3404 and tissue support structure 3402. The sharpened tip is rotated through the tissue while the tissue support rotates in an opposite direction, forcing the tissue against and to be pierced by the sharpened tip. The relative rotational motion between tissue support structure 3402 and sharpened tip 3404 provides the device operator with tactile feedback as to the amount of force being applied to a tissue.

In accordance with the principles of the present invention, tissue support structure 3402 and sharpened tip 3404 are suitably configured to approach and engage a portion of tissue from a broad range of angles or positions. Combination of the various sharpened tip configurations in accordance with the present invention and the adjustability of those tips with the tissue support structure provides an even broader range of options for engaging a tissue between a sharpened tip and tissue support structure 3402.

With continued reference to FIG. 35, a suture 302 is connected with the sharpened tip and passed through the tissue as the sharpened tip pierces the tissue. After piercing, the suture is grasped on the other side of the tissue, as described above, released from the sharpened tip, and then pulled through the tissue for further use in suturing.

Figure 36:
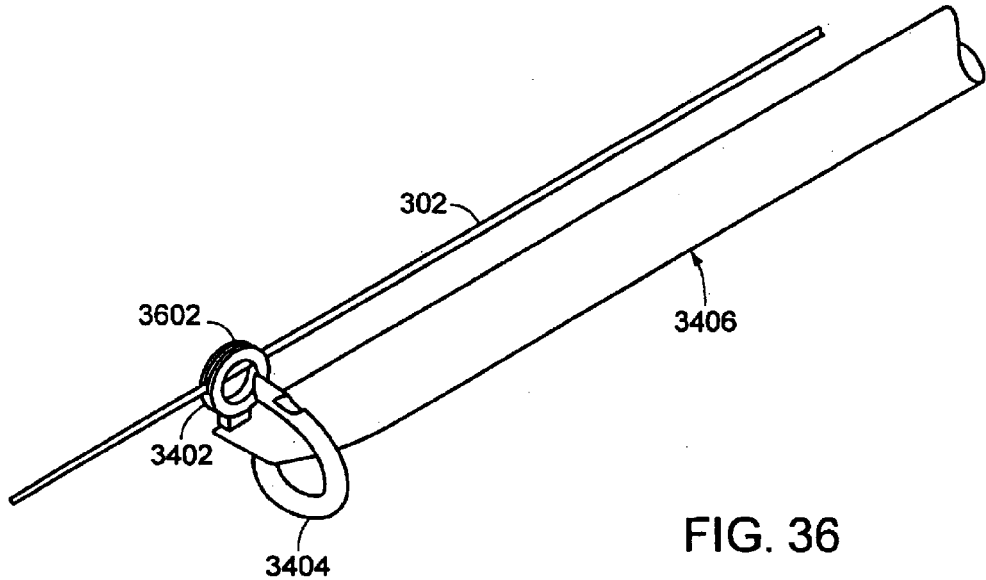

Referring now to FIG. 36, an alternative configuration for drawing a suture through a tissue is disclosed (Exhibit C is a color illustration of the elements of FIG. 36). A suture 302 is connected with a sling 3602 in a tissue support device 3604. The sharpened tip pierces the tissue with the assistance of the tissue support device, and engages the suture as the sharpened tip is drawn back through the tissue and the suturing device is rotated open. In this way, if a suture is preferably applied from a side of a tissue inaccessible to the sharpened tip, the sharpened tip may be engaged from the opposite (and accessible) side of the tissue, and then made to draw the suture back through the tissue.

The present invention has been described above with reference to preferred embodiments. However, those skilled in the art having read this disclosure will recognize that changes and modifications may be made to the preferred embodiment without departing from the scope of the present invention. For example, the combination of the various opening configurations with the configurations of the sharpened tip is clearly contemplated by this disclosure. Similarly, the use of the various eyelets, tip configurations, and locking mechanisms with the different tissue support features is intended. These and other changes or modifications are intended to be included within the scope of the present invention, as expressed in the following claims.

What is claimed is:

1. A method of delivering a suture comprising:
   providing a suture device;
   releasably coupling a suture to a distal end of the suture device by threading the suture through a first region of a bounded opening of the suture device and then moving the suture to a second region of the bounded opening having a dimension smaller than a diameter of the suture to trap the suture in the second region;
   penetrating a substrate with the distal end of the suture device such that a portion of the suture passes through the substrate; and
   releasing the suture from the distal end of the suture device while at least a portion proximal of the distal end of the suture device is penetrating the substrate.

2. The method as defined in claim 1, further comprising a second penetrating through the substrate with the distal end of the suture device prior to the releasing.

3. The method as defined in claim 1, wherein the distal end comprises a sharpened tip, a tissue support device is disposed adjacent the sharpened tip, and the penetrating a substrate comprises locating the tissue support device adjacent a selected portion of tissue and moving the sharpened tip relative to the tissue support device to facilitate penetration of the sharpened tip through the selected portion of tissue.

4. The method as defined in claim 1 wherein providing a suture device includes providing the distal end of the suture device with a curved, hook-like shape.

5. The method as defined in claim 1 further comprising wedging the suture in the second region to trap the suture.

6. The method as defined in claim 1 wherein releasing the suture comprises pulling the suture from the opening.

7. The method of claim 1 further comprising providing a tool configured to assist in releasing the suture from the distal end of the suture device.

8. A method of delivering a suture comprising:
   providing a suture device;
   releasably coupling a suture to a distal end of the suture device by threading the suture through a first region of a bounded opening of the suture device and then moving the suture to a second region of the bounded opening having a dimension smaller than a diameter of the suture to trap the suture in the second region;
   penetrating a substrate with the distal end of the suture device such that a portion of the suture passes through the substrate; and
   releasing the suture from the distal end of the suture device;
   wherein an orientation of the distal end of the suture device is selectively adjustable relative to an axis of the suture device.

9. The method as defined in claim 8 further comprising a second penetrating through the substrate with the distal end of the suture device prior to the releasing.

10. The method as defined in claim 8 wherein the distal end comprises a sharpened tip, a tissue support device is disposed adjacent the sharpened tip, and the penetrating a substrate comprises locating the tissue support device adjacent a selected portion of tissue and moving the sharpened tip relative to the tissue support device to facilitate penetration of the sharpened tip through the selected portion of tissue.

11. The method as defined in claim 8 wherein providing a suture device includes providing the distal end of the suture device with a curved, hook-like shape.

12. The method as defined in claim 8 further comprising wedging the suture in the second region to trap the suture.

13. The method as defined in claim 8 wherein releasing the suture comprises pulling the suture from the opening.

14. A method of delivering a suture comprising:
   providing a suture device;
   releasably coupling a suture to a distal end of the suture device by threading the suture through a first region of a bounded opening of the suture device and then moving the suture to a second region of the bounded opening having a dimension smaller than a diameter of the suture to trap the suture in the second region;

penetrating a substrate with the distal end of the suture device such that a portion of the suture passes through the substrate; and releasing the suture from the distal end of the suture device;

wherein the distal end of the suture device is selectively detachable from a shaft of the suture device.

15. The method as defined in claim 14, wherein the distal end of the suture device is replaceable with a differently shaped distal end.

16. The method as defined in claim 14 further comprising a second penetrating through the substrate with the distal end of the suture device prior to the releasing.

17. The method as defined in claim 14 wherein the distal end comprises a sharpened tip, a tissue support device is disposed adjacent the sharpened tip, and the penetrating a substrate comprises locating the tissue support device adjacent a selected portion of tissue and moving the sharpened tip relative to the tissue support device to facilitate penetration of the sharpened tip through the selected portion of tissue.

18. The method as defined in claim 14 wherein providing a suture device includes providing the distal end of the suture device with a curved, hook-like shape.

19. The method as defined in claim 14 further comprising wedging the suture in the second region to trap the suture.

20. The method as defined in claim 14 wherein releasing the suture comprises pulling the suture from the opening.

* * * * *